(12) United States Patent
Mertens et al.

(10) Patent No.: US 6,685,905 B2
(45) Date of Patent: Feb. 3, 2004

(54) SILICOALUMINOPHOSPHATE MOLECULAR SIEVES

(75) Inventors: Machteld M. Mertens, Boortmeerbeek (BE); Brita Engels, Betekom (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 166 days.

(21) Appl. No.: 10/074,618

(22) Filed: Feb. 13, 2002

(65) Prior Publication Data

US 2003/0153799 A1 Aug. 14, 2003

(51) Int. Cl.$^7$ ................................. C01B 37/08
(52) U.S. Cl. ................ 423/306; 423/DIG. 30; 585/640
(58) Field of Search .............. 423/306, DIG. 30; 502/214; 585/640

(56) References Cited

U.S. PATENT DOCUMENTS

| | | | |
|---|---|---|---|
| 4,440,871 A | 4/1984 | Lok et al. | 502/214 |
| 4,499,327 A | 2/1985 | Kaiser | 585/640 |
| 4,861,743 A | 8/1989 | Flank et al. | 502/214 |
| 5,096,684 A | 3/1992 | Guth et al. | 423/306 |
| 5,227,151 A | 7/1993 | Calabro | 423/703 |
| 5,324,493 A | 6/1994 | Mueller et al. | |
| 5,370,851 A | 12/1994 | Wilson | 423/305 |
| 5,514,362 A | 5/1996 | Miller | 423/702 |
| 5,609,843 A * | 3/1997 | Wendelbo | 423/306 |
| 5,879,655 A | 3/1999 | Miller et al. | 423/702 |
| 6,403,855 B1 * | 6/2002 | Mertens | 585/640 |

FOREIGN PATENT DOCUMENTS

| | | | |
|---|---|---|---|
| EP | 0293919 | 12/1988 | C01B/25/45 |
| EP | 0 391 774 | 10/1990 | C01B/33/34 |
| EP | 0541915 B1 | 7/1996 | C07C/11/02 |
| EP | 0 893 159 | 1/1999 | B01J/29/06 |
| EP | 1110911 A2 | 6/2001 | C01B/37/02 |
| WO | WO 89/01912 | 6/1989 | C01B/25/36 |
| WO | WO 94/13584 | 6/1994 | C01B/33/18 |

* cited by examiner

*Primary Examiner*—David Sample

(57) ABSTRACT

In SAPO manufacture, handling of the synthesis mixture is facilitated by providing an initial aluminium-containing aqueous slurry with an $H_2O:Al_2O_3$ weight ratio of 3:1 to 8:1.

11 Claims, No Drawings

SILICOALUMINOPHOSPHATE MOLECULAR SIEVES

CROSS REFERENCE TO RELATED APPLICATIONS

This application claims priority to European Patent Application No. EP 01310795.8, filed Dec. 21, 2001, which is fully incorporated herein by reference.

FIELD OF INVENTION

This invention relates to a process for the manufacture of silicoaluminophosphate molecular sieves.

BACKGROUND OF THE INVENTION

Silicoaluminophosphate (SAPO) molecular sieves are described in U.S. Pat. No. 4,440,871. These molecular sieves are generally classified as being microporous materials containing 8, 10 or 12-membered ring structures. These ring structures can have an average pore size ranging from about 3.5 Å to 15 Å. Small pore SAPO molecular sieves with an average pore size from about 3.5 Å to 5 Å are typical of molecular sieves containing 8-membered rings.

An important use of SAPO is the catalytic conversion of oxygenates, e.g., methanol, to olefins, especially the lighter olefins, e.g., ethylene and propylene. The global demand for ethylene and propylene is increasing and as the cost of petroleum feedstock, their traditional source, increases, the use of SAPO catalysts in oxygenate to olefin conversion has significant commercial value. Numerous references, including U.S. Pat. No. 4,499,327 and EP-A-541,915, describe the manufacture of olefins from methanol using various SAPO molecular sieve catalysts. The literature describes a number of different processes for the manufacture of SAPO's, in particular for the formation of the synthesis mixture which is to be subjected to the hydrothermal treatment typically used for the formation of the crystalline molecular sieves. In many such processes, the source of aluminium is added to an aqueous solution of the source of phosphorus, which is conveniently a strong phosphoric acid solution. The aluminium source is peptized by the phosphoric acid, a reaction that is hard to control, and results in a pasty composition difficult to handle, especially on a commercial scale.

Although the commercially most economic sources of aluminium are inorganic, many of these, for example hydrated aluminas, e.g., pseudoboehmite, have the disadvantage of not being readily soluble in water, tending to form a gel, which is also difficult to handle on a commercial scale. Although in principle these difficulties may be overcome, for example by the use of larger quantities of water, this dilutes the phosphoric acid and inhibits the process of digestion of the aluminium source.

If SAPO molecular sieves are to be used commercially, an economically acceptable way of preparing these materials in high yield and large quantities is needed. It is highly desirable that the structural and chemical properties of the product be consistent from one batch to another. The formation of an inconsistent process mixture or gel will interfere with preparing SAPO with consistent properties.

SUMMARY OF THE INVENTION

The present invention provides a process for the manufacture of a silicoaluminophosphate molecular sieve, which comprises forming a synthesis mixture by the steps of:

a) mixing an inorganic source of aluminium and water to form a mixture having a water to aluminium, measured as $Al_2O_3$, ratio within the range of 3:1 to 8:1 by weight;

b) mixing a source of phosphorus with the product of step a);

c) mixing a structure directing agent and a source of silicon with the product of step b); and d) subjecting the synthesis mixture resulting from step c) to hydrothermal treatment under conditions effective to produce the desired silicoaluminophosphate molecular sieve.

Advantageously, the $H_2O:Al_2O_3$ weight ratio of the mixture formed in step a) is within the range 3.5:1 to 6:1.

The components of the synthesis mixture are typically those known in the art or as described in the literature for the production of the SAPO concerned.

The aluminium source may be, for example, an aluminium oxide (alumina), optionally hydrated, an aluminium salt, especially a phosphate, an aluminate, or a mixture thereof. A preferred source is a hydrated alumina, most preferably pseudoboehmite, which contains about 75% $Al_2O_3$ and 25% $H_2O$ by weight.

Advantageously, the source of phosphorus is a phosphoric acid, especially orthophosphoric acid, but other sources, for example, organic phosphates, e.g., triethyl phosphate, and aluminophosphates may be used.

Advantageously, the source of silicon is silica, for example colloidal silica, famed silica, or an organic silicon source, e.g., a tetraalkyl orthosilicate, especially tetraethyl orthosilicate.

The synthesis mixture also contains a structure directing agent, or template. In general, these are organic bases, especially nitrogen-containing bases, more especially amines and quaternary ammonium compounds, used singly or in combinations. The template is chosen according to the SAPO being manufactured.

As templates there may be mentioned, for example, tetraethyl ammonium compounds, cyclopentylamine, aminomethyl cyclohexane, piperidine, triethylamine, cyclohexylamine, trimethylhydroxyethylamine, morpholine, dipropylamine (DPA), pyridine, isopropylamine and mixtures thereof. Preferred templates are triethylamine, cyclohexylamine, piperidine, pyridine, isopropylamine, tetraethyl ammonium compounds, dipropylamine, and mixtures thereof. The tetraethylammonium compounds include tetraethyl ammonium hydroxide (TEAOH), and tetraethyl ammonium phosphate, fluoride, bromide, chloride, and acetate. Preferred tetraethyl ammonium compounds are the hydroxide and the phosphate. The molecular sieve structure may be effectively controlled using combinations of templates.

Optionally, seeds of the desired SAPO or of a different molecular sieve, may be used to assist formation of the desired SAPO.

DETAILED DESCRIPTION OF THE INVENTION

The process of the invention is suitable for the manufacture of, inter alia, SAPO-5, -8, -11, -16, -17, -20, -31, -36, -37, -40, -41, -42 and -47, especially suitable for the manufacture of SAPO-35, -44 and -56, and more especially suitable for the manufacture of SAPO-18 and SAPO-34, or more generally materials of the CHA or AEI structure types. The two last-mentioned SAPO's may form as an intergrown material.

Substituted SAPOs may also be manufactured by the process of the invention. These materials are generally known as metal-containing silicoaluminophosphates or MeSAPOs. The metal may be an alkali metal (Group IA), alkaline earth metal (Group IIA), rare earth (Group IIIB, including the lanthanide elements) or the metals of Groups IB, IIB, IVB, VB, VIB, VIIB, and VIIIB. Preferably, Me represents Zn, Ni or Cu. These atoms may be incorporated into the tetrahedral framework through a $MeO_2$ tetrahedral unit, typically by adding the metal component during synthesis of the molecular sieve.

The product of step a) of the process, which is generally a slurry, is advantageously mixed with the source of phosphorus by slowly adding the phosphorus source to the aluminium-containing product. However, the product may instead be slowly added to the phosphorus source. In either case, the addition is carried out at a rate sufficiently slow to prevent the formation of a viscous gel.

Admixture of the silicon source and the template then follow, being carried out in any conventional manner.

In general, the hydrothermal treatment of the synthesis mixture to yield the desired crystalline molecular sieve is advantageously carried out under autogenous pressure, for example in an autoclave, for example a stainless steel autoclave which may, if desired, be ptfe-lined. The treatment may, for example, be carried out at a temperature within the range of from 50, advantageously from 90, especially 120, to 250° C., depending on the molecular sieve being made. The treatment may, for example, be carried out for a period within the range of from 20 to 200 hours, preferably up to 100 hours, again depending on the molecular sieve being formed. The procedure may include an ageing period, either at room temperature or, preferably, at a moderately elevated temperature, before the hydrothermal treatment at more elevated temperature. The latter may include a period of gradual or stepwise variation in temperature.

The treatment may be carried out with the vessel static or, preferably, with stirring or with rotating the vessel about a horizontal axis (tumbling). If desired, the synthesis mixture may be stirred or tumbled during an initial part of the heating stage, for example, from room temperature to an elevated, e.g., the final treatment, temperature, and be static for the remainder. Agitation generally produces a product with a smaller particle size and a narrower particle size distribution than static hydrothermal treatment.

A synthesis mixture for producing SAPO-34 according to the invention advantageously has a molar composition, apart from seeds if present, within the following ranges:

| | |
|---|---|
| $P_2O_5:Al_2O_3$ | 0.6 to 1.2:1, preferably 0.65 to 0.91:1 |
| $SiO_2:Al_2O_3$ | 0.05 to 0.5:1, preferably 0.3 to 0.5:1 |
| $H_2O:Al_2O_3$ | 10 to 100:1 | together with an organic template, advantageously tetraethylammonium hydroxide (TEAOH), dipropylamine (DPA), isopropylamine or morpholine, or a mixture of two or more such templates, in a proportion appropriate to yield SAPO-34. A preferred template mixture comprises TEAOH and DPA.

The invention also provides the use of forming an initial mixture of water and an inorganic aluminium source in a weight ratio of water to aluminium, calculated as $Al_2O_3$, within the range of 3:1 to 8:1 to facilitate handling of a silicoaluminate molecular sieve synthesis mixture.

The invention further provides the products of the process and of the use of the invention. The products, if required after cation exchange and/or calcining, have utility as catalyst precursors, catalysts, and separation and absorption media. They are especially useful in numerous hydrocarbon conversions, separations and absorptions. They may be used alone, or in admixture with other molecular sieves, in particulate form, supported or unsupported, or in the form of a supported layer, for example in the form of a membrane, for example as described in International Application WO 94/25151. Hydrocarbon conversions include, for example, cracking, reforming, hydrofining, aromatization, oligomerisation, isomerization, dewaxing, and hydrocracking (e.g., naphtha to light olefins, higher to lower molecular weight hydrocarbons, alkylation, transalkylation, disproportionation or isomerization of aromatics). Other conversions include the reaction of alcohols with olefins and the conversion of oxygenates to hydrocarbons, especially of methanol to olefins, especially light olefins. SAPO-34 produced by the process of the invention is especially suitable for this conversion.

Conversion of oxygenates may be carried out with the oxygenate, e.g., methanol, in the liquid or, preferably, the vapour phase, in batch or, preferably, continuous mode. When carried out in continuous mode, a weight hourly space velocity (WHSV), based on oxygenate, of advantageously 1 to 1000, preferably 1 to 100, hour$^{-1}$ may conveniently be used. An elevated temperature is generally required to obtain economic conversion rates, e.g., one between 300 and 600° C., preferably from 400 to 500° C., and more preferably about 450° C. The catalyst may be in a fixed bed, or a dynamic, e.g., fluidized or moving, bed.

For the conversion of oxygenates, the SAPO, advantageously SAPO-34, advantageously has a relatively low $SiO_2:Al_2O_3$ ratio, to minimize saturates formation. Advantageously a $SiO_2:Al_2O$ ratio of at most 0.4:1, preferably at most 0.32:1 and most preferably at most 0.2:1 is employed.

The oxygenate feedstock may be mixed with a diluent, inert under the reaction conditions, e.g., argon, nitrogen, carbon dioxide, hydrogen, or steam. The concentration of methanol in the feedstream may vary widely, e.g., from 5 to 90 mole per cent of the feedstock. The pressure may vary within a wide range, e.g., from atmospheric to 500 kPa.

EXAMPLES

The following Examples, in which parts are by weight unless otherwise indicated, illustrate the invention. The source and purity of starting materials are those first given, unless indicated otherwise.

COMPARATIVE EXAMPLE

Alumina, Pural SB Condea 75%, 68.06 g, was mixed with water, 100.5 g, to form an aluminium oxide slurry. The $H_2O:Al_2O_3$ weight ratio was 2.3:1. Phosphoric acid, 85%, 115.74 g, diluted with 104.92 g of water was added to the aluminium oxide slurry with stirring, at a rate of 100 ml/min. The alumina-phosphoric acid mixture was stirred for about 6 minutes following the complete addition of the acid. The $P_2O_5:Al_2O_3$ weight ratio was 1.4:1. Colloidal silica, Ludox AS40, 22.50 g, was added to the alumina-phosphoric acid mixture and stirred for 2 minutes. Water, 10.20 g, was used to rinse the remaining silica from the beaker into the mixture. Tetraethylammonium hydroxide (TEAOH), 40% in water, 183.31 g, was added and the mixture stirred for about 5 minutes. Water, 43.17 g, was used to rinse the remaining TEAOH from the beaker into the mixture. Dipropylamine (DPA), 80.79 g, was added to the mixture and stirred. Water, 26.27 g, was used to rinse the remaining DPA from the beaker into the mixture. Upon adding the DPA two phases formed, however, after several minutes a single phase white suspension was observed. Also, the suspension becomes less viscous with time, and the pH of the final mixture was between 7 and 8. The visually uniform mixture is transferred to an autoclave and heated without stirring at 175° C. for 60 hours.

The reaction mixture was cooled to ambient temperature, and the solid product recovered by filtration. The solids were washed with several small portions of water and dried at 120° C. SAPO-34 with a molar chemical composition of $Al_2O_3/0.91P_2O_5/0.35SiO_2$ was obtained. The yield of the synthesis was 12.2% based on the total weight of the initial synthesis mixture.

On repetition of this procedure using 50-fold additions of aluminium, phosphorus, and silicon, yielding a total volume of synthesis mixture greater than 40 litres, an unworkable viscous mixture was obtained.

Example 1

Alumina (Pural SB Condea 75%) 3.67 kg, was mixed with 12.6 kg of water to form an aluminium oxide slurry. The $H_2O:Al_2O_3$ weight ratio was 4.9:1. 85% phosphoric acid, 6.28 kg, was added to the aluminium oxide slurry at a rate of 6 kg/hr with continuous mixing. A viscous mixture was obtained, but stirring of the reaction mixture was possible. The $P_2O_5:Al_2O_3$ weight ratio was 1.4:1. To this mixture was added 1.22 kg of Nalco 2327 (40.2 wt % $SiO_2$). Some rinse water was used to rinse the remaining silica from the beaker into the mixture. Tetraethylammonium hydroxide (TEAOH), 10.62 g, 35% by weight in water, was added and the mixture stirred for 1 hour. Again some small amount of water was used to rinse the remaining TEAOH from the beaker into the mixture. Dipropylamine (DPA), 4.3 kg, was added over 30 minutes. At all times a homogeneous well stirrable suspension was obtained. The pH of the final mixture was between 7 and 8. The visually uniform mixture was transferred to an autoclave and heated without stirring at 175° C. for 55 hours.

The reaction mixture was cooled to ambient temperature, and the solid product recovered by filtration. The solids were washed with several small portions of water and dried at 120° C. Pure SAPO-34 was obtained in a yield of 16.2 wt % based on total initial synthesis mixture.

What is claimed:

1. A process for the manufacture of a silicoaluminophosphate molecular sieve, the process comprising:
   (i) forming a synthesis mixture comprising the steps of:
      (a) mixing an inorganic source of aluminium and water to form a first mixture having a water to aluminium, measured as $Al_2O_3$, ratio within the range of 3:1 to 8:1 by weight;
      (b) mixing a source of phosphorus with the product of step (a); and
      (c) mixing a structure directing agent and a source of silicon with the product of step (b); and
   (ii) subjecting the synthesis mixture resulting from step (c) to hydrothermal treatment under conditions effective to produce the silicoaluminophosphate molecular sieve.

2. The process of claim 1, wherein the water to aluminium ($H_2O:Al_2O_3$) ratio is within the range of 3.5:1 to 6:1.

3. The process according of claim 1, wherein the aluminium source is a hydrated alumina.

4. The process of claim 3, wherein the hydrated alumina is pseudoboehmite.

5. The process of claim 1, wherein the source of phosphorus is a phosphoric acid.

6. The process of claim 1, wherein the molecular sieve is of a CHA or an AEI structure-type.

7. The process of claim 6, wherein the molecular sieve is selected from one or more of the group consisting of: SAPO-34 and SAPO-18.

8. The process of claim 7 wherein the structure directing agent is TEAOH, or a mixture of TEAOH and DPA.

9. The process of claim 1, wherein the first mixture has a resulting volume of at least 10 litres.

10. The process of claim 1, wherein the process further comprises the step (i) washing the molecular sieve, optionally calcining or performing a cation exchange step.

11. A process for the conversion of an oxygenate to olefin(s), the process comprising: contacting the oxygenate under catalytic conversion conditions with the molecular sieve of claim 1.

* * * * *